United States Patent
Meiser et al.

(10) Patent No.: US 12,127,761 B2
(45) Date of Patent: Oct. 29, 2024

(54) SURGICAL INSTRUMENTS INCORPORATING ULTRASONIC AND ELECTROSURGICAL FUNCTIONALITY

(71) Applicant: Covidien LP, Mansfield, MA (US)

(72) Inventors: Thomas W. Meiser, Lakewood, CO (US); David J. Van Tol, Boulder, CO (US); Daniel A. Friedrichs, Aurora, CO (US); Rachael L. Kabala, Fort Collins, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/114,920

(22) Filed: Feb. 27, 2023

(65) Prior Publication Data
US 2023/0200838 A1 Jun. 29, 2023

Related U.S. Application Data

(62) Division of application No. 16/238,754, filed on Jan. 3, 2019, now Pat. No. 11,589,889.
(Continued)

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1442* (2013.01); *A61B 18/1445* (2013.01);
(Continued)

(58) Field of Classification Search
CPC .. A61B 17/320092; A61B 2017/00411; A61B 2017/2938; A61B 2017/320071;
(Continued)

(56) References Cited

U.S. PATENT DOCUMENTS

| 5,190,517 A | 3/1993 | Zieve et al. |
| 5,312,329 A | 5/1994 | Beaty et al. |

(Continued)

FOREIGN PATENT DOCUMENTS

| EP | 2322111 A1 | 5/2011 |
| EP | 2474280 A1 | 7/2012 |

(Continued)

OTHER PUBLICATIONS

Extended European Search Report issued in corresponding European Application No. 20201742.2 dated Feb. 10, 2021, 8 pages.
(Continued)

*Primary Examiner* — Khadijeh A Vahdat

(57) ABSTRACT

A surgical instrument end effector assembly includes a first jaw member defining an insulative tissue-contacting surface and first and second electrically-conductive tissue-contacting surfaces disposed on either side of the insulative surface. A second jaw member of the end effector assembly includes an ultrasonic blade body positioned to oppose the insulative surface of the first jaw member, and first and second electrically-conductive tissue-contacting surfaces disposed on either side of the ultrasonic blade body and positioned to oppose the first and second electrically-conductive surfaces, respectively, of the first jaw member. The first jaw member is movable relative to the second jaw member between a spaced-apart position and an approximated position to grasp tissue therebetween. The first and second electrically-conductive surfaces of the second jaw member are movable, independent of the first jaw member, relative to the first jaw member and the ultrasonic blade body between a retracted position and an extended position.

20 Claims, 5 Drawing Sheets

Related U.S. Application Data

(60) Provisional application No. 62/618,402, filed on Jan. 17, 2018, provisional application No. 62/618,277, filed on Jan. 17, 2018, provisional application No. 62/618,241, filed on Jan. 17, 2018, provisional application No. 62/618,292, filed on Jan. 17, 2018.

(51) Int. Cl.
  *A61B 17/00* (2006.01)
  *A61B 17/29* (2006.01)
  *A61B 18/00* (2006.01)

(52) U.S. Cl.
  CPC ........... *A61B 2017/00411* (2013.01); *A61B 2017/2938* (2013.01); *A61B 2017/320071* (2017.08); *A61B 2017/320074* (2017.08); *A61B 2017/320094* (2017.08); *A61B 2017/320095* (2017.08); *A61B 2017/320098* (2017.08); *A61B 2018/00077* (2013.01); *A61B 2018/00083* (2013.01); *A61B 2018/00184* (2013.01); *A61B 2018/00601* (2013.01); *A61B 2018/0063* (2013.01); *A61B 2018/00922* (2013.01); *A61B 2018/00994* (2013.01); *A61B 2018/1467* (2013.01); *A61B 2018/1475* (2013.01)

(58) Field of Classification Search
  CPC ....... A61B 2017/320074; A61B 2017/320094; A61B 2017/320095; A61B 2017/320098; A61B 18/1442; A61B 18/1445; A61B 2018/00077; A61B 2018/00083; A61B 2018/00184; A61B 2018/00601; A61B 2018/0063; A61B 2018/00922; A61B 2018/00994; A61B 2018/1467; A61B 2018/1475
  See application file for complete search history.

(56) References Cited

U.S. PATENT DOCUMENTS

| | | | |
|---|---|---|---|
| 5,443,463 A | 8/1995 | Stern et al. | |
| 6,251,110 B1 | 6/2001 | Wampler | |
| 6,257,241 B1 | 7/2001 | Wampler | |
| 6,416,486 B1 | 7/2002 | Wampler | |
| 6,562,032 B1 | 5/2003 | Ellman et al. | |
| 6,736,814 B2 | 5/2004 | Manna et al. | |
| 7,717,913 B2 | 5/2010 | Novak et al. | |
| 7,905,881 B2 * | 3/2011 | Masuda | A61B 17/320092 606/51 |
| 8,773,001 B2 | 7/2014 | Wiener et al. | |
| 9,700,366 B2 | 7/2017 | Paulus | |
| 11,589,889 B2 | 2/2023 | Meiser et al. | |
| 2007/0173872 A1 | 7/2007 | Neuenfeldt | |
| 2010/0145335 A1 | 6/2010 | Johnson et al. | |
| 2011/0015660 A1 | 1/2011 | Wiener et al. | |
| 2012/0150176 A1 | 6/2012 | Weizman | |
| 2014/0135804 A1 | 5/2014 | Weisenburgh, II et al. | |
| 2014/0330271 A1 | 11/2014 | Dietz | |
| 2015/0148804 A1 | 5/2015 | Rooks et al. | |
| 2015/0164533 A1 | 6/2015 | Felder et al. | |
| 2015/0182251 A1 | 7/2015 | Messerly et al. | |
| 2016/0038220 A1 | 2/2016 | Twomey | |
| 2017/0007317 A1 | 1/2017 | Allen, IV et al. | |
| 2017/0105754 A1 | 4/2017 | Boudreaux et al. | |
| 2017/0164973 A1 * | 6/2017 | Lesko | A61B 17/320092 |
| 2017/0202570 A1 | 7/2017 | Shelton, IV | |
| 2017/0202609 A1 | 7/2017 | Shelton, IV | |

FOREIGN PATENT DOCUMENTS

| | | | |
|---|---|---|---|
| EP | 2583633 A1 | 4/2013 |
| EP | 2829245 A1 | 1/2015 |
| EP | 2946737 A1 | 11/2015 |
| EP | 3117790 A1 | 1/2017 |
| WO | 9517855 A1 | 7/1995 |
| WO | 2017100423 A2 | 6/2017 |
| WO | 2017123837 A2 | 7/2017 |

OTHER PUBLICATIONS

Extended European Search Report issued in European Application No. 19152026.1 dated Jun. 28, 2019, 6 pages.
Extended European Search Report issued in European Application No. 19152133.5 dated Jun. 28, 2019, 6 pages.
Extended European Search Report issued in corresponding European Application No. 20195714.9 dated Dec. 21, 2020, 8 pages.
Extended European Search Report issued in corresponding European Application No. 19152030.3 dated Apr. 10, 2019, 8 pages.
Partial European Search Report issued in corresponding European Application No. 19152028.7 dated Apr. 12, 2019, 12 pages.
Communication Pursuant to Article 94(3) EPC issued in corresponding European Application No. 19152028.7 dated May 7, 2021, 5 pages.

* cited by examiner

SURGICAL INSTRUMENTS INCORPORATING ULTRASONIC AND ELECTROSURGICAL FUNCTIONALITY

CROSS REFERENCE TO RELATED APPLICATION

This application is a divisional application of U.S. patent application Ser. No. 16/238,754, filed on Jan. 3, 2019, now U.S. Pat. No. 11,589,889, which claims the benefit of and priority to U.S. Provisional Patent Application Nos. 62/618,241, 62/618,277, 62/618,292, and 62/618,402, all of which were filed on Jan. 17, 2018. This application is also related to U.S. patent application Ser. Nos. 16/238,600, 16/238,668, and 16/238,812, all of which were filed on Jan. 3, 2019. The entire contents of each of the above applications are hereby incorporated herein by reference.

BACKGROUND

1. Technical Field

The present disclosure relates to energy-based surgical instruments and, more particularly, to surgical instruments having end effector assemblies incorporating ultrasonic and electrosurgical functionality to facilitate treating, e.g., sealing and/or dissecting tissue.

2. Discussion of Related Art

Ultrasonic surgical devices are used in many surgical procedures. An ultrasonic surgical device may include, for example, an ultrasonic blade and a clamp mechanism to enable clamping tissue against the blade. Ultrasonic energy transmitted to the blade causes the blade to vibrate at very high frequencies (e.g., 55,500 times per second), which allows for heating tissue to treat tissue clamped against or otherwise in contact with the blade.

Electrosurgical devices are also used in many surgical procedures. An electrosurgical device may include, for example, opposing jaw members operable to clamp tissue therebetween and conduct energy, e.g., RF energy, through clamped tissue to treat tissue.

Devices that combine ultrasonic and electrosurgical energy into a single multi-functional device are known, but may not leverage the strengths of both technologies effectively. In particular, existing devices may have end effectors that are not optimized for the combined use of ultrasonic and electrosurgical energy.

SUMMARY

As used herein, the term "distal" refers to the portion that is being described that is further from a user, while the term "proximal" refers to the portion that is being described that is closer to a user. Further, to the extent consistent, any of the aspects described herein may be used in conjunction with any of the other aspects described herein.

A surgical instrument provided in accordance with aspects of the present disclosure includes an end effector assembly having first and second jaw members. The first jaw member defines an insulative tissue-contacting surface and first and second electrically-conductive tissue-contacting surfaces disposed on either side of the insulative tissue-contacting surface. The first and second electrically-conductive tissue-contacting surfaces of the first jaw member are adapted to connect to a source of electrosurgical energy. The second jaw member includes an ultrasonic blade body adapted to receive ultrasonic energy from an ultrasonic waveguide and positioned to oppose the insulative tissue-contacting surface of the first jaw member. The second jaw member further includes first and second electrically-conductive tissue-contacting surfaces adapted to connect to a source of electrosurgical energy, disposed on either side of the ultrasonic blade body, and positioned to oppose the first and second electrically-conductive tissue-contacting surfaces, respectively, of the first jaw member. The first jaw member is movable relative to the second jaw member between a spaced-apart position and an approximated position to grasp tissue therebetween. The first and second electrically-conductive tissue-contacting surfaces of the second jaw member are movable, independent of the movement of the first jaw member, relative to the first jaw member and the ultrasonic blade body between a retracted position and an extended position.

In an aspect of the present disclosure, the surgical instrument further includes a housing, a shaft extending distally from the housing, and an ultrasonic waveguide extending through the shaft. The end effector assembly is supported at a distal end portion of the shaft.

In another aspect of the present disclosure, a trigger is operably associated with the housing and coupled to the first jaw member. The trigger is selectively actuatable to move the first jaw member relative to the second jaw member between the spaced-apart position and the approximated position.

In yet another aspect of the present disclosure, an actuator is operably associated with the housing and coupled to the first and second electrically-conductive tissue-contacting surfaces of the second jaw member. The actuator is selectively actuatable to move the first and second electrically-conductive tissue-contacting surfaces of the second jaw member between the retracted position and the extended position.

In still another aspect of the present disclosure, an activation button is disposed on the housing. The activation button is selectively activatable to supply electrosurgical energy and/or ultrasonic energy to the end effector assembly.

In another aspect of the present disclosure, the first jaw member includes a jaw body and a jaw liner disposed thereon. The jaw liner defines the insulative tissue-contacting surface. The jaw liner may be formed from a compliant material.

In still yet another aspect of the present disclosure, the first and second electrically-conductive tissue-contacting surfaces are defined on first and second electrodes, respectively, of the second jaw member. The first and second electrodes are disposed on either side of the ultrasonic blade body, and positioned to oppose the first and second electrically-conductive tissue-contacting surfaces, respectively, of the first jaw member. The first and second electrodes are movable to thereby move the first and second electrically-conductive tissue-contacting surfaces of the first jaw member between the retracted position and the extended position.

In another aspect of the present disclosure, a jaw actuation frame is operably coupled to the first and second electrodes and configured to move the first and second electrodes to thereby move the first and second electrically-conductive tissue-contacting surfaces of the first jaw member between the retracted position and the extended position.

Another surgical instrument provided in accordance with aspects of the present disclosure includes an end effector assembly having first and second jaw members. The first jaw member is bifurcated into first and second jaw components defining first and second electrically-conductive tissue-contacting surfaces, respectively. The first and second electrically-conductive tissue-contacting surfaces are adapted to connect to a source of electrosurgical energy. The second jaw member includes an ultrasonic blade body adapted to receive ultrasonic energy from an ultrasonic waveguide and adapted to connect to a source of electrosurgical energy. The first and second jaw components of the first jaw member are movable relative to the second jaw member between a spaced-apart position and an approximated position to grasp tissue therebetween.

In an aspect of the present disclosure, the surgical instrument further includes a housing, a shaft extending distally from the housing, and an ultrasonic waveguide extending through the shaft. The end effector assembly is supported at a distal end portion of the shaft.

In another aspect of the present disclosure, a trigger is operably associated with the housing and coupled to the first jaw member. The trigger is selectively actuatable to move the first jaw member relative to the second jaw member between the spaced-apart position and the approximated position.

In still another aspect of the present disclosure, an activation button is disposed on the housing. The activation button is selectively activatable to supply electrosurgical energy and/or ultrasonic energy to the end effector assembly.

In yet another aspect of the present disclosure, the first and second electrically-conductive tissue-contacting surfaces are electrically-isolated from one another and energizable to different potentials for conducting electrosurgical energy therebetween. Alternatively or additionally, the first and second electrically-conductive tissue-contacting surfaces are electrically-coupled to one another and configured to conduct energy from the first and second electrically-conductive tissue-contacting surfaces to the ultrasonic blade body.

BRIEF DESCRIPTION OF THE DRAWINGS

Objects and features of the present disclosure will become apparent to those of ordinary skill in the art when descriptions thereof are read with reference to the accompanying drawings, of which.

DETAILED DESCRIPTION

Figure 1:
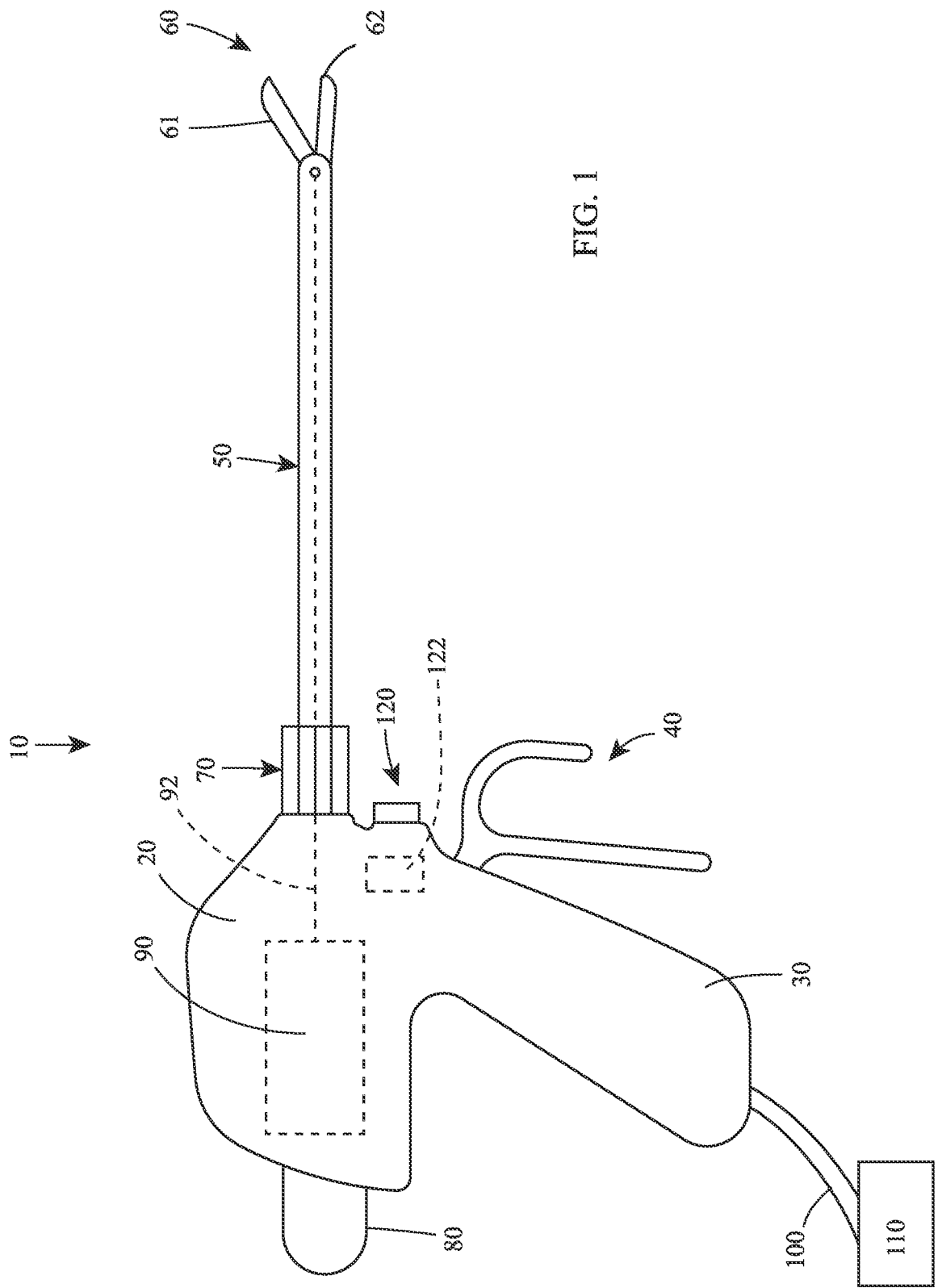
FIG. 1 is a side view of a surgical instrument exemplifying the aspects and features of the present disclosure.

Referring generally to FIG. 1, a combined electrosurgical, e.g., RF, and ultrasonic surgical instrument exemplifying the aspects and features of the present disclosure is shown and generally identified by reference numeral 10. For the purposes herein, surgical instrument 10 is generally described. Aspects and features of surgical instrument 10 not germane to the understanding of the present disclosure are omitted to avoid obscuring the aspects and features of the present disclosure in unnecessary detail.

Surgical instrument 10 generally includes a housing 20, a handle 30, a trigger 40, an elongated shaft 50, an end effector assembly 60, a rotating assembly 70, an actuator 80, an ultrasonic transducer 90, a cable 100 coupled to a surgical generator 110, and an activation switch 120. Activation switch 120 selectively activates a supply of electrosurgical energy from generator 110 to end effector 60 for treating tissue in an electrosurgical energy mode and selectively activates a supply of ultrasonic energy from ultrasonic transducer 90 (powered by generator 110) to end effector assembly 60 for treating tissue in an ultrasonic energy mode. To accomplish this, a switch box 122 disposed within housing 20 and coupled to actuator 80, activation switch 120, and/or generator 110 may be provided to determine the mode of surgical instrument 10 and enable the supply of the appropriate energy depending upon the mode. Alternatively, separate switches may be provided for each mode. Further, as an alternative to a separate generator 110, a generator and battery may be incorporated on or within housing 20 such that surgical instrument 10 operates as a cordless device.

With continued reference to FIG. 1, elongated shaft 50 of surgical instrument 10 extends distally from housing 20 and supports end effector assembly 60 at a distal end portion of elongated shaft 50. End effector assembly 60 is disposed at the distal end portion of elongated shaft 50 and includes first and second jaw members 61, 62, respectively, that cooperate to clamp and treat tissue, as described in further detail below. Rotating assembly 70 enables the selective rotation of elongated shaft 50 and, thus, end effector assembly 60 relative to housing 20. Actuator 80 is selectively manipulatable in any suitable fashion, e.g., rotated, pivoted, translated, combinations thereof, etc. to transition end effector assembly 60 between an ultrasonic configuration for use in the ultrasonic energy mode and an electrosurgical configuration for use in the electrosurgical energy mode. In embodiments where end effector assembly 60 need not be physically transitioned between the ultrasonic and electrosurgical energy modes, actuator 80 may be omitted.

Handle 30 is integrally associated with housing 20 for clamping and/or handling surgical instrument 10. Trigger 40 is movable relative to handle 30 from an initial position to an actuated position. Trigger 40 is operably coupled to a drive assembly (not shown) that mechanically imparts movement to end effector assembly 60. More specifically, actuation of trigger 40 causes first jaw member 61 to pivot relative to second jaw member 62 from a spaced-apart position to an approximated position to clamp tissue therebetween.

End effector assembly 60, as noted above, includes first and second jaw members 61, 62. Generally, in an ultrasonic mode, when activation switch 120 is activated, second jaw member 62 serves as an ultrasonic blade that is acoustically coupled to ultrasonic transducer 90 via a waveguide 92 to enable transmission of ultrasonic energy from ultrasonic transducer 90, along waveguide 92, to second jaw member 62 for treating tissue. In an electrosurgical mode, when activation switch 120 is activated, electrodes on one or both of the jaw members 61, 62 are energized to enable the conduction of electrosurgical energy through tissue clamped between jaw members 61, 62 to treat tissue. Various embodiments of end effector configurations suitable for use with surgical instrument 10 for the above purposes are described in detail below with reference to FIGS. 2A-3B. To the extent consistent, any of the aspects and features of the embodiments detailed below may be incorporated into any of the other embodiments.

Figure 2B:
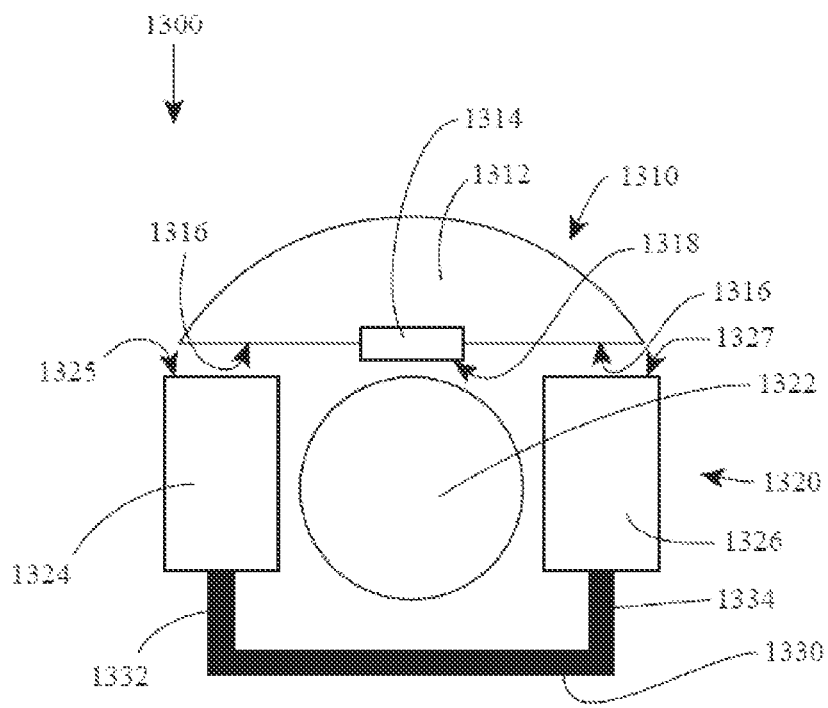
FIG. 2B is a transverse, cross-sectional view of the end effector assembly of FIG. 2A, in a second configuration.
Figure 2A:
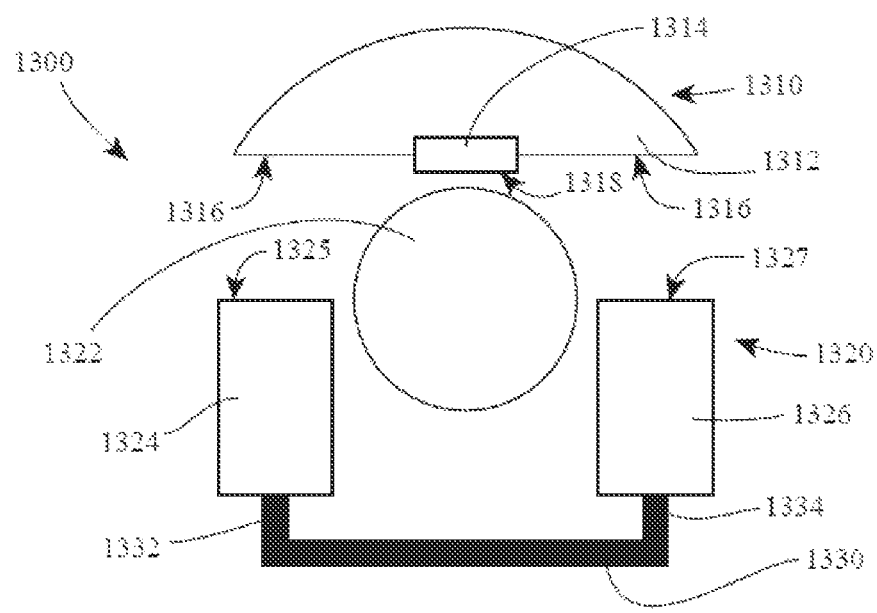
FIG. 2A is a transverse, cross-sectional view of an end effector assembly configured for use with the surgical instrument of FIG. 1, in a first configuration.
Figure 3A:
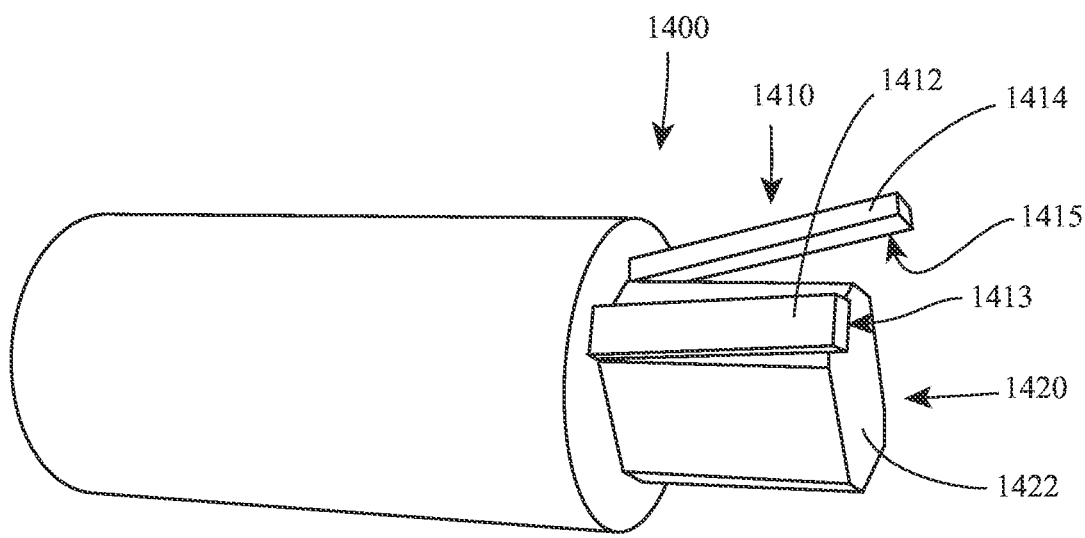
FIG. 3A is a side, perspective view of another end effector assembly configured for use with the surgical instrument of FIG. 1.
Figure 3B:
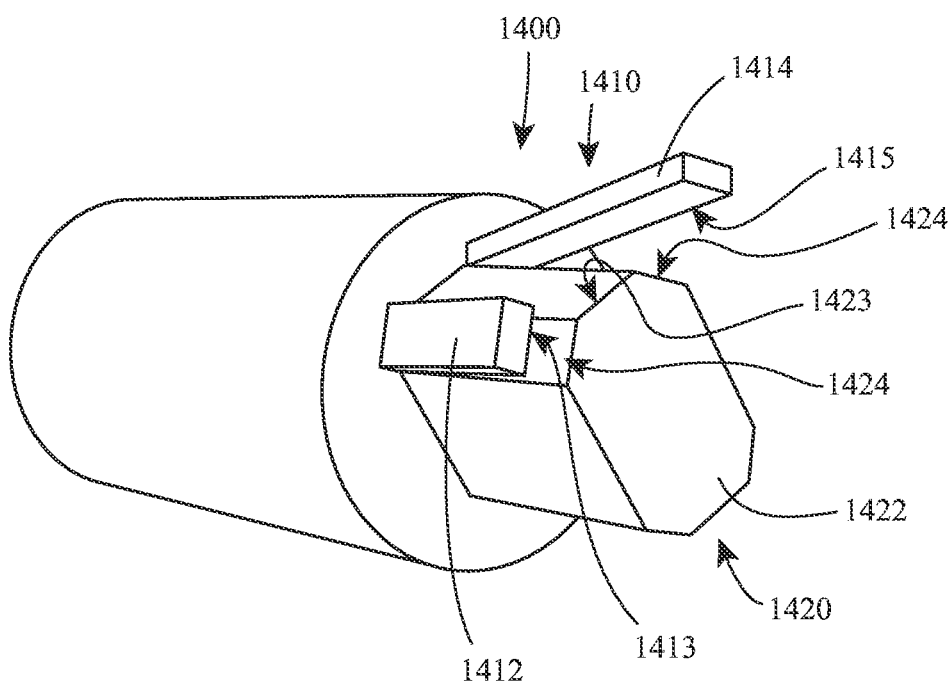
FIG. 3B is a front, perspective view of the end effector assembly of FIG. 3A.

Referring now to FIGS. 2A and 2B, in conjunction with FIG. 1, another end effector assembly 1300 is provided in accordance with the present disclosure. End effector assembly 1300 includes first and second jaw members 1310, 1320, respectively. First jaw member 1310 includes a jaw body 1312 and a jaw liner 1314 engaged to jaw body 1312. Jaw body 1312 defines a tissue-contacting surface 1316 on either side of jaw liner 1314. Jaw liner 1314 also defines a tissue-contacting surface 1318. Jaw liner 1314 may protrude from jaw body 1312 towards jaw members 1320 (as shown), may be recessed relative to jaw body 1312, or may be substantially co-planar therewith. Jaw liner 1314 may be formed from an insulative, compliant material, e.g., PTFE. Tissue-contacting surfaces 1316 of jaw body 1312, on the other hand, are at least partially formed from or include electrically-conductive material disposed thereon that is electrically coupled to generator 110 and activation switch 120, e.g., via one or more lead wires (not shown) extending through cable 100, housing 20, and elongated shaft 50, and may be energized to similar or different potentials.

Jaw member 1320 includes an ultrasonic blade body 1322, a pair of jaw component 1324, 1326 surrounding ultrasonic blade body 1322, and an actuation frame 1330. Ultrasonic blade body 1322 is configured to receive ultrasonic energy from waveguide 92 for treating tissue clamped between ultrasonic blade body 1322 and jaw liner 1314 of jaw member 1310 in the ultrasonic energy mode.

Jaw components 1324, 1326 are disposed on either side of ultrasonic blade body 1322 and are electrically coupled to generator 110 and activation switch 120, e.g., via one or more lead wires (not shown) extending through cable 100, housing 20, and elongated shaft 50. Jaw components 1324, 1326 define tissue-contacting surfaces 1325, 1327 configured to oppose tissue-contacting surfaces 1316 of jaw member 1310 and conduct electrosurgical energy therebetween in the electrosurgical energy mode. Tissue-contacting surfaces 1325, 1327 may be energized to similar or different potentials.

Actuation frame 1330 of jaw member 1320 includes first and second wedges 1332, 1334 disposed adjacent and supporting jaw components 1324, 1326, respectively. Actuation frame 1330 is operably coupled to actuator 80 by way of linkages, connectors, and/or other suitable structures, such that actuation of actuator 80, e.g., distal urging of actuator 80 relative to housing 20, urges actuation frame 1330 distally such that first and second wedges 1332, 1334 are moved distally to cam jaw components 1324, 1326 from a retracted position (FIG. 2A), wherein jaw components 1324, 1326 are recessed relative to ultrasonic blade body 1322, to an extended position (FIG. 2B), wherein jaw components 1324, 1326 extend to or beyond ultrasonic blade body 1322 towards jaw member 1310. Upon proximal movement of first and second wedges 1332, 1334, e.g., upon proximal return of actuator 80 relative to housing 20, jaw components 1324, 1326 are returned to the retracted position.

The retracted position (FIG. 2A) corresponds to an ultrasonic energy mode, wherein ultrasonic blade body 1322 is aligned with jaw liner 1314 such that, upon activation, ultrasonic energy is transmitted along waveguide 92 to ultrasonic blade body 1322 for treating tissue clamped between ultrasonic blade body 1322 and jaw liner 1314.

The extended position (FIG. 2B) corresponds to a combined or electrosurgical energy mode, wherein ultrasonic blade body 1322 is aligned with jaw liner 1314 and jaw components 1324, 1326 are positioned adjacent tissue-contacting surfaces 1316 of jaw body 1312 of jaw member 1310 in the approximated position. With jaw members 1310, 1320 in the approximated position clamping tissue therebetween, and jaw components 1324, 1326 disposed in the extended position, jaw component 1324 and the tissue-contacting surface 1316 on the same side may be energized to a first potential, while jaw component 1326 and the tissue contacting surface 1316 on the same side are energized to a second, different potential such that electrosurgical energy is conducted transversely through tissue to seal tissue clamped between jaw members 1310, 1320. Alternatively, jaw components 1324, 1326 may be energized to the same potential and tissue contacting surfaces 1316 energized to a different potential such that electrosurgical energy is conducted therebetween to create two tissue seals, one on either side of ultrasonic blade body 1322. In still another alternative, jaw components 1324, 1326 and tissue contacting surfaces 1316 can be energized at one potential with the ultrasonic blade body 1322 being energized at a different potential such that electrosurgical energy is conducted transversely through tissue to seal tissue clamped between jaw members 1310, 1320. In any of these configurations, ultrasonic energy may be transmitted to ultrasonic blade body 1322 (simultaneously, overlapping, or consecutively with the supply of electrosurgical energy), to dissect the sealed tissue or tissue between the two tissue seals.

Referring now to FIGS. 3A-4B, in conjunction with FIG. 1, another end effector assembly 1400 in accordance with the present disclosure is shown. End effector assembly 1400 generally includes a first jaw member 1410 and a second jaw member 1420. First jaw member 1410 is bifurcated into jaw components 1412, 1414 that are spaced-apart and electrically isolated from one another. Jaw components 1412, 1414 are electrically coupled to generator 110 and activation switch 120, e.g., via one or more lead wires (not shown) extending through cable 100, housing 20, and elongated shaft 50, and may be energized to similar or different potentials.

Jaw member 1420 is an ultrasonic blade body 1422 that is acoustically coupled to waveguide 92 to enable transmission of ultrasonic energy from ultrasonic transducer 90, along waveguide 92, to ultrasonic blade body 1422. Ultrasonic blade body 1422 is also electrically coupled to generator 110 and activation switch 120, e.g., via one or more lead wires (not shown) extending through cable 100, housing 20, and elongated shaft 50, to enable ultrasonic blade body 1422 to be energized with electrosurgical energy.

Ultrasonic blade body 1422 defines a generally rectangular configuration having chamfered corners such that ultrasonic blade body 1422 includes a central tissue-contacting surface 1423 and a pair of angled tissue-contacting surfaces 1424, with one of the angled tissue-contacting surfaces 1424 disposed on either side of central tissue-contacting surface 1423. Angled tissue-contacting surfaces 1424 may be angled relative to central tissue-contacting surface 1423 such as, for example, at an angle of 20 degrees to 70 degrees, in embodiments, at an angle of 30 degrees to 60 degrees, in embodiments, or, in still other embodiments, of about 45 degrees wherein (the "about" takes into account manufacturing, material, and other tolerances).

Jaw components 1412, 1414 define tissue-contacting surfaces 1413, 1415, respectively, and are angled relative to one another and ultrasonic blade body 1422 of second jaw member 1420 such as, for example, at an angle of 20 degrees to 70 degrees, in embodiments, at an angle of 30 degrees to 60 degrees, in embodiments, or, in still other embodiments, of about 45 degrees wherein (the "about" takes into account manufacturing, material, and other tolerances).

Figure 4A:
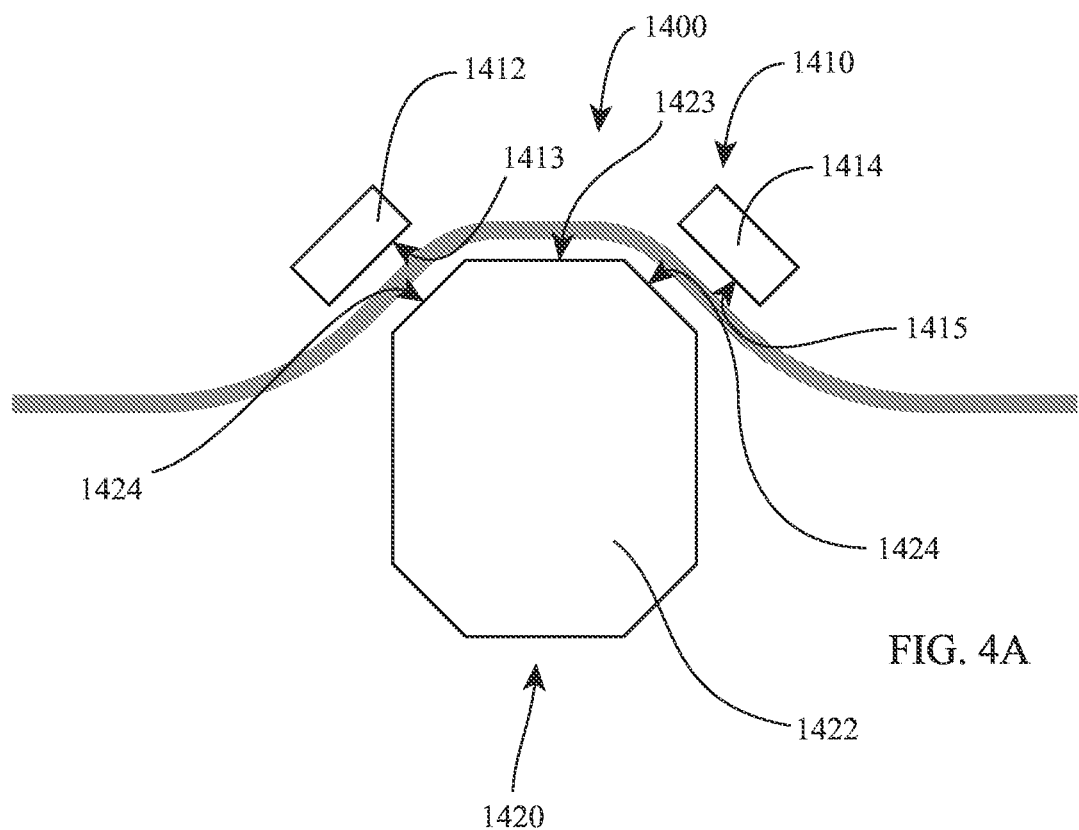
FIG. 4A is a transverse, cross-sectional view of the end effector assembly of FIG. 3A grasping tissue.
Figure 4B:
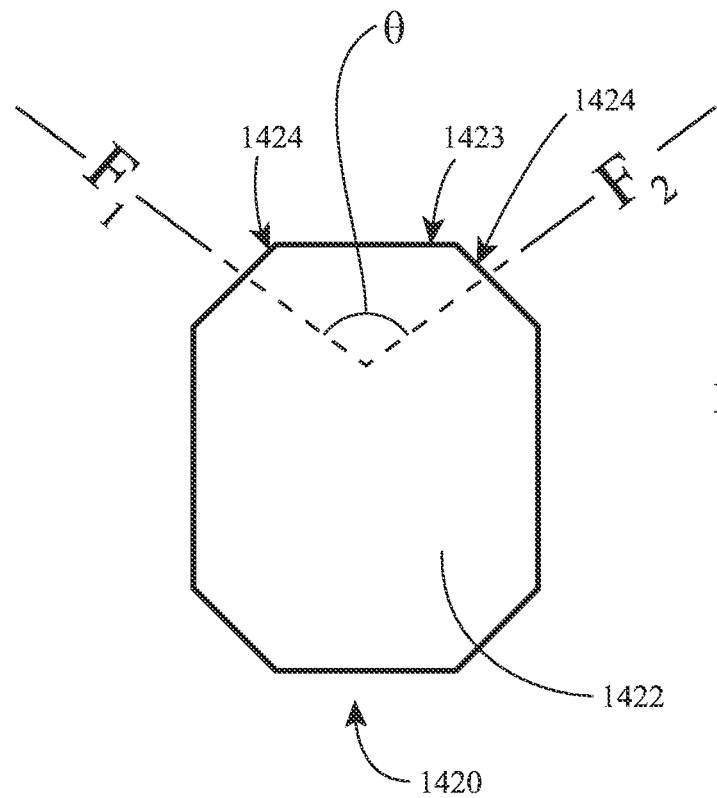
FIG. 4B is a force diagram of the end effector assembly of FIG. 3A.

Jaw components 1412, 1414, more specifically, are disposed at similar angles as opposed angled tissue-contacting surfaces 1424 of ultrasonic blade body 1422 such that tissue-contacting surfaces 1413, 1415 are disposed in generally parallel orientation (where "generally" takes into account manufacturing, material, and other tolerances) relative to the opposed angled tissue-contacting surfaces 1424 of ultrasonic blade body 1422 in the approximated position of end effector assembly 1400. Thus, as illustrated in FIG. 4B, the clamping force applied from jaw components 1412, 1414 to ultrasonic blade body 1422 are normal to the respective angled tissue-contacting surfaces 1424 of ultrasonic blade body 1422.

In embodiments, jaw components 1412, 1414 are configured to reduce the application of forces to ultrasonic probe body 1422 that could potentially damage ultrasonic probe body 1422. For example, tissue-contacting surfaces 1413, 1415 of jaw components 1412, 1414 may define an angle of 90 degrees or less therebetween (such that the angle "θ," the angle between the direction of applied force from each jaw component 1412, 1414, is at or above 90 degrees). As a result, that no more than one half of the applied force from jaw components 1412, 1414 is applied downwardly to ultrasonic probe body 1422, while the rest of the force is applied inwardly to "squeeze" ultrasonic probe body 1422. This reduction in downward force, particular in high force applications, helps inhibit damage such as cracking to ultrasonic probe body 1422 and/or enables ultrasonic probe body 1422 to be formed from a smaller-cross-sectional dimension (which increases dissection capability and reduces thermal injury), while still providing sufficient strength to withstand the forces of jaw components 1412, 1414.

In operation, trigger 40 is actuated to move jaw members 1410, 1420 to the approximated position to clamp tissue therebetween. With jaw members 1410, 1420 in the approximated position clamping tissue therebetween, jaw components 1412, 1414 may be energized to different potentials, while ultrasonic blade body 1422 remains neutral, such that electrosurgical energy is conducted transversely through tissue to seal tissue clamped between jaw members 1410, 1420. Alternatively, jaw components 1412, 1414 may be energized to the same potential and ultrasonic blade body 1422 may be energized to a different potential such that electrosurgical energy is conducted therebetween to create two tissue seals, one on either side of ultrasonic blade body 1422. In either configuration, ultrasonic energy may be transmitted to ultrasonic blade body 1422 (simultaneously, overlapping, or consecutively with the supply of electrosurgical energy), to dissect the sealed tissue or tissue between the two tissue seals.

In embodiments, jaw components 1412, 1414 may be independently movable to enable sealing with only one jaw component 1412, 1414, on one side of ultrasonic blade body 1422, e.g., for sealing smaller tissues. Alternatively, jaw components 1412, 1414 may be coupled to move in conjunction with one another; or a selector (not shown) may be provided to enable transitioning between an independent mode and a coupled mode.

Figure 5:
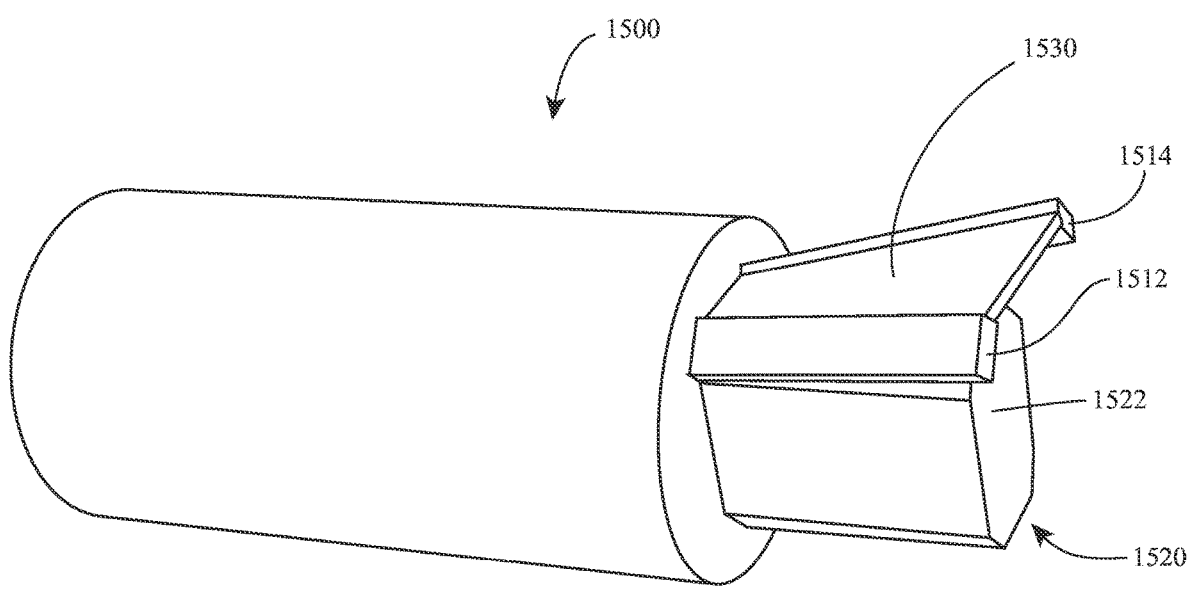
FIG. 5 is a perspective view of yet another end effector assembly configured for use with the surgical instrument of FIG. 1.

Turning now to FIG. 5, another end effector assembly 1500 in accordance with the present disclosure is shown. End effector assembly 1500 generally includes a first jaw member 1510 and a second jaw member 1520. First jaw member 1510 is bifurcated into jaw components 1512, 1514 that are spaced-apart and electrically isolated from one another. Jaw components 1512, 1514 are electrically coupled to generator 110 and activation switch 120, e.g., via one or more lead wires (not shown) extending through cable 100, housing 20, and elongated shaft 50, and may be energized to similar or different potentials.

Jaw member 1520 is an ultrasonic blade body 1522 that is acoustically coupled to waveguide 92 to enable transmission of ultrasonic energy from ultrasonic transducer 90, along waveguide 92, to ultrasonic blade body 1522. Ultrasonic blade body 1522 is also electrically coupled to generator 110 and activation switch 120, e.g., via one or more lead wires (not shown) extending through cable 100, housing 20, and elongated shaft 50, to enable ultrasonic blade body 1422 to be energized with electrosurgical energy.

End effector assembly 1500 is similar to end effector assembly 1400 (FIGS. 3A-4B), except that end effector assembly 1500 further includes a flexible coupling 1530 interconnecting jaw components 1512, 1514 with one another. Thus, jaw components 1412, 1414 are configured to move in conjunction with one another and are not capable of independent movement.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A surgical instrument, comprising:
   an end effector assembly, including:
   a first jaw member, including:
   an insulative tissue-contacting surface; and
   first and second electrically-conductive tissue-contacting surfaces disposed on either side of the insulative tissue-contacting surface, the first and second electrically-conductive tissue-contacting surfaces adapted to connect to a source of electrosurgical energy; and
   a second jaw member, including:
   an ultrasonic blade body adapted to receive ultrasonic energy from an ultrasonic transducer and positioned to oppose the insulative tissue-contacting surface of the first jaw member; and
   first and second electrically-conductive tissue-contacting surfaces adapted to connect to the source of electrosurgical energy, disposed on either side of the ultrasonic blade body, and positioned to oppose the first and second electrically-conductive tissue-contacting surfaces, respectively, of the first jaw member,
   wherein the first jaw member is movable relative to the second jaw member between a spaced-apart position and an approximated position to grasp tissue therebetween, and
   wherein the first and second electrically-conductive tissue-contacting surfaces of the second jaw member are movable, independent of the movement of the first jaw member, relative to the first jaw member and the ultrasonic blade body between a retracted position and an extended position.

2. The surgical instrument according to claim 1, further comprising:
   a housing;

a shaft extending distally from the housing; and
an ultrasonic waveguide extending through the shaft,
wherein the end effector assembly is supported at a distal end portion of the shaft.

3. The surgical instrument according to claim 2, further comprising a trigger operably associated with the housing and coupled to the first jaw member, the trigger selectively actuatable to move the first jaw member relative to the second jaw member between the spaced-apart position and the approximated position.

4. The surgical instrument according to claim 2, further comprising an actuator operably associated with the housing and coupled to the first and second electrically-conductive tissue-contacting surfaces of the second jaw member, the actuator selectively actuatable to move the first and second electrically-conductive tissue-contacting surfaces of the second jaw member between the retracted position and the extended position.

5. The surgical instrument according to claim 2, further comprising an activation button disposed on the housing, the activation button selectively activatable to supply at least one of electrosurgical energy or ultrasonic energy to the end effector assembly.

6. The surgical instrument according to claim 2, further comprising an activation button disposed on the housing, the activation button selectively activatable to supply both electrosurgical energy and ultrasonic energy to the end effector assembly.

7. The surgical instrument according to claim 1, wherein the first jaw member includes a jaw body and a jaw liner disposed thereon, the jaw liner defining the insulative tissue-contacting surface.

8. The surgical instrument according to claim 7, wherein the jaw liner is formed from a compliant material.

9. The surgical instrument according to claim 1, wherein the first and second electrically-conductive tissue-contacting surfaces are defined on first and second electrodes, respectively, of the second jaw member, the first and second electrodes disposed on either side of the ultrasonic blade body, and positioned to oppose the first and second electrically-conductive tissue-contacting surfaces, respectively, of the first jaw member, the first and second electrodes movable to thereby move the first and second electrically-conductive tissue-contacting surfaces of the first jaw member between the retracted position and the extended position.

10. The surgical instrument according to claim 9, further including a jaw actuation frame operably coupled to the first and second electrodes and configured to move the first and second electrodes to thereby move the first and second electrically-conductive tissue-contacting surfaces of the first jaw member between the retracted position and the extended position.

11. A surgical instrument, comprising:
an end effector assembly, including:
an ultrasonic blade body adapted to connect to a source of ultrasonic energy for transmitting ultrasonic energy to tissue to treat tissue;
a jaw member movable relative to the ultrasonic blade body between a spaced-apart position and an approximated position to grasp tissue therebetween, and
at least one jaw component movable, independent of the movement of the jaw member, relative to the ultrasonic blade body between a retracted position, wherein the at least one jaw component is recessed relative to the ultrasonic blade body, and an extended position, wherein the at least one jaw component is aligned with or protrudes beyond the ultrasonic blade body towards the jaw member,
wherein at least one of the ultrasonic blade body, the jaw member, or the at least one jaw component is adapted to connect to a source of electrosurgical energy for transmitting electrosurgical energy to tissue to treat tissue.

12. The surgical instrument according to claim 11, wherein at least two of the ultrasonic blade body, the jaw member, or the at least one jaw component are adapted to connect to a source of electrosurgical energy for transmitting electrosurgical energy to tissue to treat tissue.

13. The surgical instrument according to claim 11, wherein at least one of the jaw member, the ultrasonic blade body, or the at least one jaw component is configured to be energized with electrosurgical energy at a first potential and wherein at least one other of the jaw member, the ultrasonic blade body, or the at least one jaw component is configured to be energized with electrosurgical energy at a second different potential to conduct electrosurgical energy between the first and second potentials and through tissue to treat tissue.

14. The surgical instrument according to claim 11, further comprising an insulator disposed on the jaw member and positioned to oppose the ultrasonic blade body in the approximated position of the jaw member.

15. The surgical instrument according to claim 14, wherein at least one of the jaw member, the ultrasonic blade body, the first jaw component, or the second jaw component is configured to be energized with electrosurgical energy at a first potential and wherein at least one other of the jaw member, the ultrasonic blade body, the first jaw component, or the second jaw component is configured to be energized with electrosurgical energy at a second different potential to conduct electrosurgical energy between the first and second potentials and through tissue to treat tissue.

16. The surgical instrument according to claim 15, wherein the at least one jaw component includes first and second jaw components disposed on either side of the ultrasonic blade body.

17. The surgical instrument according to claim 11, further comprising:
a housing; and
a shaft extending distally from the housing,
wherein the end effector assembly is supported at a distal end portion of the shaft.

18. The surgical instrument according to claim 17, further comprising an ultrasonic transducer supported by the housing, the ultrasonic transducer operably coupled to the ultrasonic blade body and configured to supply ultrasonic energy to the ultrasonic blade body.

19. The surgical instrument according to claim 11, further comprising a first actuator operably coupled to the jaw member and a second actuator operably coupled to the at least one jaw component.

20. The surgical instrument according to claim 11, further comprising an activation switch configured to be activated in a first mode wherein at least ultrasonic energy is transmitted to tissue to treat tissue and in a second mode wherein at least electrosurgical energy is transmitted to tissue to treat tissue.

* * * * *